United States Patent [19]

Wells et al.

[11] Patent Number: 5,104,642
[45] Date of Patent: Apr. 14, 1992

[54] HAIR STYLING COMPOSITIONS CONTAINING PARTICULAR HAIR STYLING POLYMERS AND NON-AQUEOUS SOLVENTS

[75] Inventors: Robert L. Wells, Cincinnati, Ohio; Bonnie T. King, Alexandria, Ky.; Michael A. Snyder; Donald H. Frey, both of Cincinnati, Ohio

[73] Assignee: The Procter & Gamble Company, Cincinnati, Ohio

[21] Appl. No.: 506,409

[22] Filed: Apr. 6, 1990

[51] Int. Cl.$^5$ .................. A61K 7/075; A61K 7/08
[52] U.S. Cl. ........................ 424/47; 424/970; 424/71; 424/DIG. 1; 424/DIG. 2; 252/DIG. 13
[58] Field of Search ............ 424/47, 70, 71, 78, 424/DIG. 1, DIG. 2; 252/DIG. 13

[56] References Cited

U.S. PATENT DOCUMENTS

| | | | |
|---|---|---|---|
| 2,816,882 | 12/1957 | Schiller | 526/307.7 |
| 2,834,763 | 5/1958 | Halpern et al. | 526/245 |
| 2,996,471 | 8/1961 | Reiter | 424/47 |
| 3,072,536 | 1/1963 | Pye | 167/85 |
| 3,222,329 | 12/1965 | Grosser et al. | 260/80.5 |
| 3,405,084 | 10/1968 | Bohac | 260/29.6 |
| 3,445,566 | 5/1969 | Skoultchi | 424/17 |
| 3,577,517 | 5/1971 | Kubot et al. | 424/47 |
| 3,743,715 | 7/1973 | Viout et al. | 424/47 |
| 3,810,977 | 5/1974 | Levine | 424/47 |
| 3,907,984 | 9/1975 | Calvert et al. | 424/47 |
| 3,927,199 | 12/1975 | Miccelli | 424/47 |
| 3,936,513 | 2/1976 | Lorenz et al. | 525/379 |
| 4,012,501 | 3/1977 | Farber | 424/47 |
| 4,030,512 | 6/1977 | Papantoniou et al. | 132/7 |
| 4,067,839 | 1/1978 | Schultz | 526/916 |
| 4,151,333 | 4/1979 | Lenke et al. | 526/307.7 |
| 4,165,367 | 8/1979 | Chakrabarti | 424/47 |
| 4,192,861 | 3/1980 | Micchelli | 424/47 |
| 4,196,190 | 4/1980 | Gehman et al. | 424/47 |
| 4,223,009 | 9/1980 | Chakrabarti | 424/47 |
| 4,272,511 | 6/1981 | Papantoniou et al. | 424/47 |
| 4,283,384 | 8/1981 | Jacquet et al. | 424/47 |
| 4,374,825 | 2/1983 | Bolich, Jr. et al. | 424/70 |
| 4,387,090 | 6/1983 | Bolich, Jr. | 424/70 |
| 4,388,436 | 6/1983 | Chen | 524/553 |
| 4,548,990 | 10/1985 | Mueller et al. | 526/320 |
| 4,798,721 | 1/1989 | Yahagi et al. | 424/70 |
| 4,842,852 | 6/1989 | Nowak | 424/71 |
| 4,886,660 | 12/1989 | Patel | 424/70 |
| 4,963,348 | 10/1990 | Bolich, Jr. et al. | 424/DIG. 2 |

FOREIGN PATENT DOCUMENTS

| | | | |
|---|---|---|---|
| 116207 | 8/1984 | European Pat. Off. | |
| 1195050 | 6/1965 | Fed. Rep. of Germany | 526/307.7 |
| 60-229909 | 11/1985 | Japan | 526/307.7 |
| 60-250015 | 12/1985 | Japan | |
| 0833995 | 5/1981 | U.S.S.R. | 526/307.7 |
| 467402 | 6/1937 | United Kingdom | 526/307.7 |
| 764409 | 12/1956 | United Kingdom | 526/307.7 |
| 2155788 | 10/1985 | United Kingdom | |

OTHER PUBLICATIONS

Technical Leaflet-Luviskol VA grades-12/84.
Technical Leaflet-Luviskol VAP grades-2/84.
Encyclopedia of Polymer Science & Engineering, vol. 7, pp. 531–544, John Wiley and Sons, 1987.
Copending Applications, Ser. No. 285,137, Torgerson, filed Dec. 16, 1988.
Copending Application, Ser. No. 433,409, Bolich Jr. et al., filed Nov. 3, 1989.
Copending Application, Ser. No. 379,516, Torgerson, filed July 13, 1989.
Copending Application, Ser. No. 506,410, Wells et al., filed Apr. 6, 1990.
Copending Application, Ser. No. 506,407, Wells et al., filed Apr. 6, 1990.

Primary Examiner—Thurman K. Page
Assistant Examiner—Susan S. Rucker
Attorney, Agent, or Firm—Leonard W. Lewis; Steven J. Goldstein

[57] ABSTRACT

The present invention relates to hair styling compositions comprising from about 0.2% to about 20% of certain hair styling polymers, from about 0.2% to about 20% of certain non-aqueous solvents for said hair styling polymers, and the balance, an aqueous base; wherein the hair styling polymer and the solvent therefor are dispersed as a separate fluid phase in the aqueous base of the hair styling composition.

20 Claims, No Drawings

HAIR STYLING COMPOSITIONS CONTAINING PARTICULAR HAIR STYLING POLYMERS AND NON-AQUEOUS SOLVENTS

TECHNICAL FIELD

The present invention relates to hair styling compositions which provide unique hair styling benefits. These are achieved by utilizing hair styling compositions having certain hair styling polymers and solvents for said polymers dispersed in an aqueous base as a separate fluid phase.

BACKGROUND OF THE INVENTION

In washing, drying and styling one's hair several end results are desired. Firstly, and most obviously, one desires that the hair be thoroughly cleaned. Most desirable is a hair care process which maintains the look and feel of clean hair between hair washings. Also in the cleaning and styling process, one desires hair conditioning providing ease of combing, relief from static electricity, manageability, and soft hair feel.

Finally, one desires a hair care process or product that provides hair styling benefits, especially hair style achievement and hold. The desire to have hair retain a particular shape is widely held. Such style retention is generally accomplished by either of two routes: permanent chemical alteration or temporary alteration of hair style/shape. A temporary alteration is one which can be removed by water or by shampooing. Temporary style alteration has generally been accomplished by means of the application of a third separate composition or compositions to dampened hair after shampooing and/or conditioning. The materials used to provide setting benefits have generally been resins or gums and have been applied in the form of mousses, gels, lotions, or sprays. The compositions are most often applied to hair dampened with water; then combed or spread through the hair by other means; followed by letting the hair dry or blow drying the hair.

The set given will vary depending on the materials used. Temporary set hair styling products typically utilize adhesive polymers which are ethanol or water-soluble rigid polymers having glass transition temperatures well above the temperatures experienced in styling hair. Examples of such high glass transition temperature adhesion polymers are found in Viout and Papantoniou U.S. Pat. 3,743,715, issued July 3, 1973; Chakrabarti U.S. Pat. No. 4,165,367, issued Aug. 21, 1979; and Chakrabarti U.S. Pat. No. 4,223,009, issued Sept. 16, 1980; the disclosures of which are incorporated by reference herein. These adhesive polymers are typically applied to the hair in an ethanol or water solvent, and then set to form rigid welds between hair fibers when the solvent evaporates as the hair dries. These hair fiber welds form the basis for the style hold ability of conventional hair styling products. When these welds are broken, they remain broken unless the appropriate polymer solvent is added to redissolve the adhesive and reform the welds when the hair dries.

In addition, many polymers said to be useful in hair styling products are multi-component polymers which combine three, four, and even more monomers into the polymer chains. Frequently, one of the monomer components is vinyl pyrrolidone. Examples of such complex polymer systems are found in Grosser et al. U.S. Pat. No. 3,222,329, issued Dec. 7, 1965; Kubot U.S. Pat. No. 3,577,517, issued May 4, 1971; Farber U.S. Pat. No. 4,012,501, issued Mar. 15, 1977; and Papantoniou and Mondet U.S. Pat. No. 4,272,511, issued June 9, 1981; the disclosures of which are incorporated by reference herein.

Other polymers said to be useful for hair styling compositions have been disclosed, such as block copolymers. These block polymers have two or more glass transition temperatures. Examples of such block polymer systems are found in Calvert et al. U.S. Pat. No. 3,907,984, issued Sept. 23, 1975; Papantoniou et al. U.S. Pat. No. 4,030,512, issued June 21, 1977; and Jacquet et al. U.S. Pat. No. 4,283,384, issued Aug. 11, 1981; the disclosures of which are incorporated by reference herein.

This traditional hair styling approach presents significant drawbacks to the user. Since the style hold is provided by resin materials which set-up on the hair, the hair tends to feel sticky or stiff after application, and it is difficult to restyle the hair without further application of the styling composition. Furthermore, since the resin materials tend to be water or ethanol-soluble, under high humidity conditions the resins become very sticky, resulting in loss of hair style and hold benefits.

Notwithstanding the great effort already put forth to identify adhesive polymers for use in temporary set hair styling products, there remains a continuing need to identify new agents which are useful to provide improved temporary set and other desirable properties to hair.

It has now been discovered that optimum hair styling and hold benefits can be achieved by utilizing hair styling compositions which comprise certain hair styling polymers, certain solvents for said hair styling polymers, and an aqueous base, wherein the polymer/solvent mixture is dispersed in the aqueous base as a separate phase.

It has now been discovered that the hair styling compositions of the present invention provide ease of hair styling achievement.

It has also been discovered that the hair styling compositions of the present invention provide good style retention benefits without leaving hair with a stiff or sticky/tacky feel.

It has also been discovered that the aforementioned products provide some degree of restyling benefit to the hair.

Hence, it is an object of the present invention to formulate hair styling compositions which provide improved hair styling benefits.

It is a further object of the present invention to provide an improved method for styling hair.

These and other objects will become readily apparent from the detailed description which follows.

SUMMARY OF THE INVENTION

The present invention relates to hair styling compositions comprising:
a. from about 0.2% to about 20% of a hair styling polymer comprising:
   A. from 0% to about 50% of a polymerizable hydrophilic monomer ($M_A$), or mixtures thereof; and
   B. from about 50% to about 100% of a polymerizable hydrophilic monomer ($M_B$), or mixtures thereof;
said polymer having a molecular weight of from about 5000 to about 1,000,000, a Tg of greater than about $-20°$ C., and a solubility parameter, $\delta$, of from about 8.5 to about 12.0;

b. from about 0.2% to about 20% of a non-aqueous solvent which will solubilize said polymer, said solvent having a boiling point of less than or equal to about 300° C., and a solubility in water at 25° C. of greater than 0.2%; and c. the balance, an aqueous carrier; wherein the polymer and solvent are present in the hair styling composition as a dispersed fluid phase; and wherein the ratio of polymer to solvent is from about 10:90 to about 80:20.

DETAILED DESCRIPTION OF THE INVENTION

The essential, as well as the optional, components of the present invention are described below.

Styling Agents

The styling compositions of the present invention contain, as an essential component, certain hair styling polymers. It is this component that provides hair styling benefits to the user.

A wide variety of hair setting polymers are generally known for use as styling agents. Examples of polymer systems are found in Grosser et al. U.S. Pat. No. 3,222,329, issued Dec. 7, 1965; Kubot et al. U.S. Pat. No. 3,577,517, issued May 4, 1971; Farber U.S. Pat. No. 4,012,501, issued Mar. 15, 1977; Papantoniou and Mondet U.S. Pat. No. 4,272,511, issued June 9, 1981; and Gehman et al. U.S. Pat. No. 4,196,190; issued Apr. 1, 1980.

Other polymers said to be useful for hair styling compositions are block polymers such as are found in Calvert et al. U.S. Pat. No. 3,907,984, issued Sept. 23, 1975; Papantoniou et al. U.S. Pat. No. 4,030,512, issued June 21, 1977; and Jacquet et al. U.S. Pat. No. 4,283,384, issued Aug. 11, 1981.

It has now been found that styling polymers having water-solubilities within a certain range provide optimum hair styling benefits when delivered from an aqueous-based hair styling composition. The styling polymers of the present invention are of relatively low water-solubility. More specifically, these polymers have a solubility parameter, $\delta$, of between about 8.5 and about 12.0 (units equal $(cal/cm^3)^{\frac{1}{2}}$), preferably from about 9.5 to about 11.5, most preferably from about 11 to about 11.5.

The solubility parameter is defined in the Polymer Handbook 3rd Ed. (John Wiley and Sons, New York), J. Brandrup and E. H. Immergut, Chapter VII, pp. 519–559, as the square root of the cohesive energy density and describes the attractive strength between molecules of the material. Solubility parameters may be determined by direct measurement, correlations with other physical properties, or indirect calculation. The solubility parameters of the present polymers were determined by indirect calculations of group contributions as described in section 2.3 on p. 524–526 of the cited reference.

It has been found that styling polymers having water solubilities within this range can be dispersed with the polymer solvent, as described infra, in aqueous-based styling compositions as a dispersed fluid phase. Styling polymers having solubility parameters at the upper end of this range would be soluble by themselves in the present styling compositions. It has now been found that when these polymers are combined with the polymer solvents of the present invention (as defined infra) and then dispersed in the styling composition, they remain in the composition as a dispersed fluid phase. Polymers having solubility parameters greater than about 12.0 will be soluble in the styling composition (even when they are premixed with the present polymer solvents). Styling polymers having solubility parameters lower than about 8.5 are difficult to remove from hair and tend to build up on hair with repeated application.

Formulation of styling compositions in this way has been shown to provide optimized hair styling benefits. The present invention allows for the use of hair styling polymers, in aqueous based hair styling compositions, which are less water-soluble than those typically used in such compositions. These polymers can be dispersed in aqueous based hair styling compositions with the use of certain compatible styling polymer solvents. These styling polymers provide optimum styling benefits in terms of ease of styling, as well as style maintenance. Because they are more hydrophobic than typical styling polymers, the present polymers do not become sticky under high humidity conditions. Furthermore, use of such polymers provides the user with some degree of restyling benefit. That is, after the present compositions are applied to the hair and the hair styled, the hair "remembers" the style after being subjected to a force, such as combing, brushing or simply flattening of the hair.

The present styling polymers must comprise at least one polymerizable hydrophobic monomer. The polymer may be a homopolymer or a copolymer of hydrophobic monomers. Alternatively, the present styling polymers may be a copolymer of a hydrophilic monomer and a hydrophobic monomer, or mixtures thereof. Hence, the present hair styling polymers comprise from 0% to about 50% of a polymerizable hydrophilic monomer ($M_A$) or mixtures thereof, and from about 50% to about 100% of a polymerizable hydrophobic monomer ($M_B$), or mixtures thereof. Of course, if the styling polymer comprises both $M_A$ monomer and $M_B$ monomer, then the monomers must be copolymerizable with each other.

Preferred hydrophilic monomers of the present styling polymers include acrylic acid, methacrylic acid, N,N-dimethylacrylamide, dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (produced by the hydrolysis of vinyl acetate after polymerization), vinyl caprolactam, and mixtures thereof.

Preferred hydrophobic monomers include acrylic or methacrylic acid esters of $C_1$-$C_{18}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, and the like, the alcohols having from about 1-18 carbon atoms with the average number of carbon atoms being from about 4-12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene;

vinyl toluene; methoxyethyl methacrylate; and mixtures thereof.

Optimum performance of the present hair styling polymers in terms of style hold has been found when the weight average molecular weight of the styling polymer is between about 5,000 and about 1,000,000, preferably between about 10,000 and about 200,000 and the glass transition temperature, Tg, (i.e., the temperature at which the polymer changes from a brittle vitreous state to a plastic state) of the styling polymer is greater than about −20° C., preferably between about 0° C. and about 80° C., and most preferably between about 20° C. and about 60° C.

Specific styling polymers of the present invention which provide the desired styling benefits are as follows: vinyl pyrrolidone/vinyl acetate copolymers (at ratios of up to about 30%, by weight, vinyl pyrrolidone); vinyl acetate homopolymer; t-butyl acrylate homopolymer; t-butyl styrene/ethyl hexyl methacrylate copolymer (50/50, by weight); dimethyl acrylamide/t-butyl acrylate/ethyl hexyl methacrylate copolymer (10/45/45); ethylene/vinyl acetate copolymer (12.5/87.5); allyl alcohol/styrene copolymer (19/81); vinyl chloride/vinyl acetate copolymer (83/17 and lower); vinyl pyrrolidone/vinyl acetate/butyl acrylate copolymer (10/78/12 and 10/70/20); vinyl pyrrolidone/vinyl acetate/butyl acrylate/styrene sulfonate copolymer (10/70/15/5); vinyl pyrrolidone/vinyl propionate copolymer (5/95); vinyl caprolactam/vinyl acetate copolymer (5/95); and styling resins sold under the trade names Ultrahold 8 ® by Ciba Geigy (ethyl acrylate/acrylic acid/N-t-butyl acrylamide copolymer), Resyn 28-1310 ® by National Starch and Luviset CA 66 ® by BASF (vinyl acetate/crotonic acid copolymer 90/10); Luviset CAP ® by BASF (vinyl acetate/vinyl propionate/crotonic acid 50/40/10); and Resyn 28-2930 ® by National Starch (vinyl acetate/vinyl neodecanoate/crotonic acid copolymer). The most preferred copolymers for use in the present invention are copolymers of vinyl pyrrolidone and vinyl acetate containing at most 30% vinyl pyrrolidone.

The polymer styling agent is present in the compositions of the present invention at a level of from about 0.2% to about 20%, preferably at a level of from about 2% to about 6%. At levels below about 0.2% styling polymer, the present hair style hold benefits cannot be achieved.

Polymer Solvent

A second essential component of the present styling compositions is a non-aqueous solvent of diluent for the styling polymer. The solvent is necessary for dilution of the polymer so that it can be dispersed in the aqueous carrier base. The present solvents aid in delivering style achievement by making polymer deposited on the hair more tacky through the hair drying and styling process. Hence, the polymer remains adhered to the hair and it enables easy manipulation of the hair into the desired style. The particular polymer chosen for use in the present conditioner compositions must be soluble in the particular solvent utilized. This enables the dispersion of the polymer/solvent mixture as a dispersed fluid phase in the aqueous-based styling composition and maintenance of that dispersed second phase. Hence, the polymer solvents of the present invention have a solubility in water at 25° C. of greater than 0.2%, preferably greater than about 0.5%, and as high as 100% soluble in water, but preferably less than 10% soluble in water.

Some solvents which are completely water-soluble will not remain as a dispersed fluid phase with the polymer in the styling composition. They will instead enter the aqueous carrier base and destroy the dispersed phase of polymer and solvent in the styling composition. Many of the solvent materials of the present invention, if dispersed alone in the aqueous carrier base of the present styling compositions, would be soluble. However, it has been found that when the solvents of the present invention are premixed with certain polymers of the present invention, prior to dispersion in the styling composition, they will remain in the polymer phase, i.e., unsolubilized in the aqueous carrier base.

The polymer solvent must also be volatile. Upon deposition of the polymer/solvent mixture on the hair, the solvent is volatilized leaving only the styling polymer on the hair, thus providing the maximum styling benefits. Generally, the polymer solvents of the present invention have a boiling point of less than or equal to about 300° C.

Additionally, the polymer solvent must not interact with the polymer styling agent in such a way that would substantially reduce the ability of the polymer to provide styling benefits to hair under ordinary use situations. The solvents must, of course, be of sufficiently high purity and sufficiently low toxicity to render them suitable for administration to human hair.

The present more hydrophilic solvents are desirable for use in hair styling compositions because they are safe to use, tend to have more aesthetically pleasing physical attributes, and because they tend to be less costly than other polymer solvents.

Specific polymer solvent materials that have been found to be useful in the present invention include isopropanol, butyl alcohol, amyl alcohol, phenyl ethanol, benzyl alcohol, ethyl butyrate, isopropyl butyrate, phenyl ethyl dimethyl carbinol, and mixtures thereof. Preferred solvents for use herein are benzyl alcohol, ethyl butyrate, phenyl ethanol, phenyl ethyl dimethyl carbinol, and mixtures thereof.

The amount of solvent to be used in the present styling compositions is an amount sufficient to solubilize the polymer and disperse it as a separate fluid phase in the aqueous carrier base. Generally, from about 0.2% to about 20%, preferably from about 2% to about 6%, polymer solvent is used. At levels below about 0.2% solvent, the styling polymer cannot be sufficiently diluted. The ratio of polymer to solvent in the present compositions is from about 10:90 to about 80:20, preferably from about 40:60 to about 60:40.

European Patent Publications 0320218, published June 14, 1989, and 0323715, published July 12, 1989, disclose certain hair styling polymers and solvents therefor, useful in hair care compositions, including shampoos and rinse-off hair conditioners. EPO Patent Publication 0323715 teaches polymer and solvent systems having very low water solubilities (polymer is less than 0.1% soluble in water, diluent is less than 0.2% soluble in water) which are dispersed as a separate fluid phase in hair care compositions.

The hair styling compositions herein can contain a variety of other optional components suitable for rendering such compositions more cosmetically or aesthetically acceptable or to provide them with additional usage benefits. Such conventional optional ingredients are well-known to those skilled in the art, e.g., opacifiers; preservatives, such as benzyl alcohol, Glydant, Kathon, methyl paraben, propyl paraben and imidazolidinyl urea; sodium chloride; sodium sulfate; polyvinyl alcohol; ethyl alcohol; pH adjusting agents, such as citric acid, sodium citrate, succinic acid, phosphoric acid, monosodium phosphate, disodium phosphate, sodium hydroxide, and sodium carbonate; coloring agents, such as any of the FD&C or D&C dyes; perfumes; sequestering agents, such as disodium ethylenediamine tetra-acetate; and polymer plasticizing agents, such as glycerin and propylene glycol. Such optional ingredients generally are used individually at levels of from about 0.01% to about 10.0%, preferably from about 0.05% to about 5.0%, of the styling composition.

As will all compositions, the present invention should not contain optional components which unduly interfere with the hair style holding performance of the present styling compositions.

The compositions of the present invention can be formulated to provide a variety of product types. These will include styling agents that are applied to and left on the hair, such as hair tonics, gels, or sprays. Also covered are rinse-off hair styling products which are applied to the hair, for example, while one is showering, and then rinsed from the hair. The polymer and solvent will be deposited onto the hair and remain thereon through the rinsing process.

In order to maintain the dispersed phase of polymer/solvent in the aqueous base of some of the compositions of the present invention (e.g., low viscosity composition) it may be necessary to include emulsifiers and/or resuspending agents to the compositions. Any typical emulsifiers (such as nonionic, anionic, zwitterionic, amphoteric or cationic surfactants) or suspending agents are usable.

The present styling compositions, if formulated as a hair styling gel, will also comprise thickeners and viscosity modifiers, such as diethanolamide of a long chain fatty acid (e.g., PEG 3 lauric diethanolamide), lauramide DEA, cocomonoethanol amide, dimethicone copolyols, guar gum, xanthan gum, methyl cellulose, hydroxyethyl cellulose, starches and starch derivatives, and polyacrylic acid. Such thickeners will also help to maintain the dispersion of polymer/solvent in the composition's base.

The balance of the present styling compositions comprises water or water combined with some other carrier substance which does not interfere with the styling benefits of the present compositions. Generally, the present styling compositions comprise from about 60% to about 99.6% of water.

The hair styling compositions of the present invention can be made using conventional formulation and mixing techniques. The polymer must first be dissolved in the polymer solvent. The remaining ingredients are combined in a separate vessel and the polymer/solvent mixture is added. Methods of making various types of hair styling compositions are described in the following examples.

Method of Use

The hair styling compositions of the present invention are used in conventional ways to provide the hair styling benefits of the present invention. Such method generally involves application of an effective amount of the styling product to wet or dry hair. By "effective amount" is meant an amount sufficient to provide the hair style benefits desired considering the length and texture of the hair. After the hair is treated with the compositions of the present invention, the hair is styled in the usual ways of the user.

The following examples illustrate the present invention. It will be appreciated that other modifications of the present invention within the skill of those in the cosmetic composition formulation art can be undertaken without departing from the spirit and scope of this invention.

All parts, percentages, and ratios herein are by weight unless otherwise specified.

EXAMPLE I

The following is an aqueous based hair styling tonic composition representative of the present invention.

| Component | Weight % |
| --- | --- |
| Styling Polymer/Solvent Premix | |
| Polyvinylpyrrolidone/Vinyl Acetate (5/95) | 3.00 |
| Benzyl Alcohol | 3.00 |
| Polysorbate 80 | 0.20 |
| Perfume | 0.10 |
| Hydroxypropylmethyl cellulose | 0.40 |
| Preservative | 0.30 |
| Water q.s. to | 100% |

This product is prepared by first dissolving the polyvinylpyrrolidone/vinyl acetate (5/95) copolymer in the benzyl alcohol. The remaining components are combined in a separate vessel with heating and stirring. The polymer/solvent mixture is then added to the remaining components either hot or after they have been cooled.

This styling tonic product provides optimum hair styling and style maintenance benefits.

EXAMPLE II

The following is an aqueous based hair styling gel composition representative of the present invention.

| Component | Weight % |
| --- | --- |
| Styling Polymer/Solvent Premix | |
| Poly t-Butyl Acrylate (MW = 100,000) | 1.50 |
| Ethyl n-Butyrate | 2.50 |
| Carbomer 941[1] | 0.30 |
| Aminomethyl Propanol | 0.10 |
| Kathon CG | 0.04 |
| Water q.s. to | 100% |

[1]Thickener available from B. F. Goodrich Co.

This product is prepared by first dissolving the poly-t-butyl acrylate in the ethyl n-butyrate. The remaining components are combined in a separate vessel with heating and stirring. The polymer/solvent mixture is then added to the remaining components either hot or after they have been cooled.

This styling gel product provides optimum hair styling and style maintenance benefits.

EXAMPLE III

The following is an aqueous based hairspray composition representative of the present invention.

| Component | Weight % |
| --- | --- |
| Styling Polymer/Solvent Premix | |
| Polyvinylpyrrolidone/vinyl acetate (30/70) | 4.0 |
| Isopropanol | 5.0 |
| Carbopol 1342[1] | 0.2 |

-continued

| Component | Weight % |
| --- | --- |
| Triethanolamine | 0.1 |
| Glydant[2] | 0.4 |
| Water q.s. to | 100% |

[1]Available from B. F. Goodrich Chemical Co.
[2]Available from Glyco Chem. Co.

This product is prepared using the method described in Example I.

This hairspray product provides optimum hair styling and style maintenance benefits.

What is claimed is:

1. A hair styling composition comprising:
   a. from about 0.2% about 20% of a hair styling polymer comprising:
      A. from 0% to about 50% of a polymerizable hydrophilic monomer ($M_A$), or mixtures thereof; and
      B. from about 50% to about 100% of a polymerizable hydrophobic monomer ($M_B$), or mixtures thereof; said polymer having a weight average molecular weight of from about 5000 to about 1,000,000, a Tg of greater than about $-20°$ C., and a solubility parameter, $\delta$, of from about 8.5 to about 12.0;
   b. from about 0.2% to about 20% of a non-aqueous solvent which will solubilize said polymer, said solvent having a boiling point of less than or equal to about 300° C., and a solubility in water at 25° C. of greater than 0.2%; and
   c. the balance, an aqueous carrier;
wherein the polymer and solvent are present in the hair styling composition as a dispersed fluid phase; and wherein the ratio of polymer to solvent is from about 10:90 to about 80:20.

2. The hair styling composition of claim 1 wherein the hair styling polymer is selected from the group consisting of vinyl pyrrolidone/vinyl acetate copolymer; t-butyl acrylate homopolymer; t-butyl styrene-/ethyl hexyl methacrylate copolymer (50/50); dimethyl acrylamide/t-butyl acrylate/ethyl hexyl methacrylate copolymer (10/45/45); ethylene/vinyl acetate copolymer (12.5/87.5); styrene/allyl alcohol copolymer (81/19); vinyl chloride/vinyl acetate copolymer (83/17 and lower); vinyl pyrrolidone/vinyl acetate/butyl acrylate copolymer (10/78/12 and 10/70/20); vinyl pyrrolidone/vinyl acetate/butyl acrylate/styrene sulfonate copolymer (10/70/17/5); vinyl pyrrolidone/vinyl propionate copolymer (5/95); vinyl caprolactam/vinyl acetate copolymer (5/95); ethyl acrylate/acrylic acid/N-t-butyl acrylamide copolymer; vinyl acetate/crotonic acid copolymer 90/10; vinyl acetate/vinyl propionate/crotonic acid 50/40/10; vinyl acetate/vinyl neodecanoate/crotonic acid copolymer; and mixtures thereof.

3. A method for providing styling benefits to hair, said method comprising applying to the hair the hair styling composition of claim 1.

4. The hair styling composition of claim 1 wherein the hair styling polymer is present in the composition at a level of from about 2% to about 6%.

5. The hair styling composition of claim 4 wherein the hair styling polymer is a vinyl pyrrolidone/vinyl acetate copolymer.

6. The hair styling composition of claim 5 wherein the solvent for the hair styling polymer is selected from the group consisting of benzyl alcohol, ethyl butyrate, phenyl ethanol, phenyl ethyl dimethyl carbinol, and mixtures thereof.

7. The hair styling composition of claim 7 wherein the solvent is soluble in water at 25° C. at greater than about 0.5%.

8. The hair styling composition of claim 7 wherein the level of solvent is from about 2% to about 6%.

9. The hair styling composition of claim 8 wherein the solvent for the hair styling polymer is selected from the group consisting of iso-propanol, butyl alcohol, amyl alcohol, phenyl ethanol, benzyl alcohol, ethyl butyrate, iso-propyl butyrate, phenyl ethyl dimethyl carbinol, and mixtures thereof.

10. The hair styling composition of claim 9 wherein the ratio of polymer to solvent is from about 40:60 to about 60:40.

11. The hair styling composition of claim 1 wherein $\delta$ is from about 9.5 to about 11.5.

12. The hair styling composition of claim 11 wherein $\delta$ is from about 11 to about 11.5.

13. The hair styling composition of claim 12 wherein the hydrophobic monomer is selected from the group consisting of acrylic acid esters of $C_1$–$C_{18}$ alcohols; methyacrylic acid esters of $C_1$–$C_{18}$ alcohols; styrene; polystyrene macromer, vinyl acetate; vinyl chloride; vinylidene chloride; vinyl propionate; alphamethylstyrene; t-butylstyrene; butadiene; cyclohexadiene; ethylene; propylene; vinyl toluene; methoxy ethyl methacrylate; and mixtures thereof.

14. The hair styling composition of claim 12 wherein the hair styling polymer comprises both the polymerizable hydrophilic monomer and the polymerizable hydrophobic monomer.

15. The hair styling composition of claim 14 wherein the hydrophilic monomer is selected from the group consisting of acrylic acid, methacrylic acid, N,N-dimethylacrylamide, dimethylaminoethyl methacrylate, methacrylamide, N-t-butyl acrylamide, maleic acid, maleic anhydride, half esters of maleic anhydride, crotonic acid, itaconic acid, acrylamide, acrylate alcohols, hydroxyethyl methacrylate, vinyl pyrrolidone, vinyl ethers, maleimides, vinyl pyridine, vinyl imidazole, styrene sulfonate, allyl alcohol, vinyl alcohol, vinyl caprolactam, and mixtures thereof.

16. The hair styling composition of claim 15 wherein the hydrophobic monomer is selected from the group consisting of acrylic acid esters of $C_1$–$C_{18}$ alcohols; methacrylic acid esters of $C_1$–$C_{18}$ alcohols; styrene; polystyrene macromer; vinyl acetate; vinyl chloride; vinylidene chloride; vinyl propionate; alphamethylstyrene; t-butylstyrene; butadiene; cyclohexadiene; ethylene; propylene; vinyl toluene; methoxy ethyl methacrylate; and mixtures thereof.

17. A hair styling composition comprising:
   a. from about 2% to about 6% of a hair styling polymer selected from polyvinyl pyrrolidone/vinyl acetate copolymers, having a weight average molecular weight of from about 10,000 to about 200,000, a Tg of from about 20° C. to about 60° C., and a solubility parameter, $\delta$, of from about 11 to about 11.5;
   b. from about 2% to about 6% of a non-aqueous solvent which will solubilize said polymer selected from the group consisting of benzyl alcohol, ethyl butyrate, phenyl ethanol, phenyl ethyl dimethyl carbinol, and mixtures thereof; and
   c. the balance, an aqueous carrier;

wherein the polymer and solvent are present in the styling composition as a dispersed fluid phase, and the ratio of polymer to solvent is from about 40:60 to about 60:40.

18. A method for providing styling benefits to hair, said method comprising applying to the hair the hair styling composition of claim 16.

19. A hair styling composition comprising:
a. from about 2% to about 6% of a hair styling polymer selected from t-butyl acrylate homopolymers, having a weight average molecular weight of from about 10,000 to about 200,000, and a Tg of from about 20° C. to about 60° C.;
b. from about 2% to about 6% of a non-aqueous solvent which will solubilize said polymer selected from the group consisting of benzyl alcohol, ethyl butyrate, phenyl ethanol, phenyl ethyl dimethyl carbinol, and mixtures thereof; and
c. the balance, an aqueous carrier;

wherein the polymer and solvent are present in the styling composition as a dispersed fluid phase, and the ratio of polymer to solvent is from about 40:60 to about 60:40.

20. A method for providing styling benefits to hair, said method comprising applying to the hair the hair styling composition of claim 19.

* * * * *